United States Patent
Zinnes et al.

[11] 3,931,230
[45] Jan. 6, 1976

[54] 3-SUBSTITUTED ISOTRYPTAMINE DERIVATIVES AND PROCESS FOR THEIR PRODUCTION

[75] Inventors: Harold Zinnes, Rockaway; Martin L. Schwartz, Gillette, both of N.J.

[73] Assignee: Warner-Lambert Company, Morris Plains, N.J.

[22] Filed: Apr. 12, 1974

[21] Appl. No.: 460,397

[52] U.S. Cl. ............... 260/326.15; 260/293.55; 260/326.12 R; 260/326.14 R; 424/274
[51] Int. Cl.² ............................ C07D 209/14
[58] Field of Search ............ 260/326.12 R, 326.15

[56] References Cited
UNITED STATES PATENTS

| | | | |
|---|---|---|---|
| 2,883,394 | 4/1959 | Schindler | 260/326.15 |
| 3,781,299 | 12/1973 | Yamamoto | 260/326.15 |

*Primary Examiner*—Lewis Gotts
*Assistant Examiner*—S. P. Williams
*Attorney, Agent, or Firm*—Albert H. Graddis; Frank S. Chow

[57] ABSTRACT

The present invention concerns compounds of Formula I

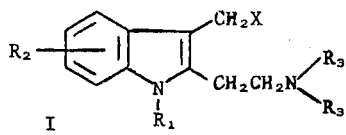

wherein $R_1$ is hydrogen, lower alkyl, aralkyl; $R_2$ is hydrogen, lower alkyl, lower alkoxy, halogen, trifluoromethyl, cyano, nitro, and the like; $R_3$ is lower alkyl; X is CN,

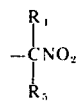

(where $R_4$ and $R_5$ are lower alkyl),

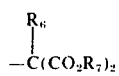

(where $R_6$ is hydrogen, lower alkyl, aryl, acetamido and $R_7$ is lower alkyl),

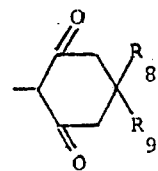

(where $R_8$ and $R_9$ are hydrogen or lower alkyl), —CH-$(SO_2C_6H_5)_2$,

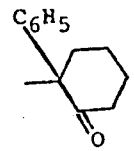

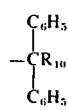

(where $R_{10}$ is hydrogen, CN, acyl),

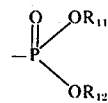

(where $R_{11}$ and $R_{12}$ are lower alkyl), $-SO_2C_6H_5$, $-CONH_2$, $-CO_2R_{13}$ (where $R_{13}$ is lower alkyl),

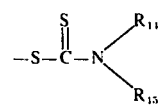

($R_{14}$ and $R_{15}$ are lower alkyl).

These compounds are useful as sedatives and antiaggression agents.

3 Claims, No Drawings

3-SUBSTITUTED ISOTRYPTAMINE DERIVATIVES AND PROCESS FOR THEIR PRODUCTION

The present invention relates to compounds of Formula I

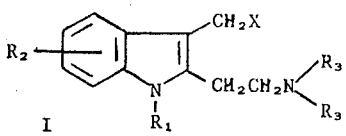

I wherein $R_1$ is hydrogen, lower alkyl, aralkyl; $R_2$ is hydrogen, lower alkyl, lower alkoxy, halogen, trifluoromethyl, cyano, nitro and the like; $R_3$ is lower alkyl, X is CN,

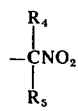

(where $R_4$ and $R_5$ are lower alkyl),

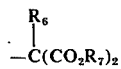

(where $R_6$ is hydrogen, lower alkyl, aryl, acetamido and $R_7$ is lower alkyl),

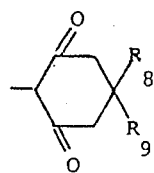

(where $R_8$ and $R_9$ are hydrogen or lower alkyl), —CH(SO$_2$C$_6$H$_5$)$_2$,

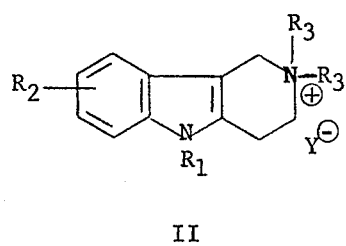

(where $R_{10}$ is hydrogen, CN, acyl),

(where $R_{11}$ and $R_{12}$ are lower alkyl), —SO$_2$C$_6$H$_5$, —CONH$_2$, —CO$_2$R$_{13}$ (where $R_{13}$ is lower alkyl),

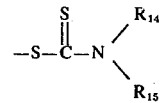

($R_{14}$ and $R_{15}$ are lower alkyl).

In the above definitions for $R_1$ to $R_{15}$, the terms "lower alkyl" and "lower alkoxy" includes lower aliphatic hydrocarbons having one to seven carbon atoms. It includes straight-chain as well as branched-chain radicals. These are, for example, methyl, propyl, isopropyl and so on. The term "aryl" means a monocyclic aromatic hydrocarbon preferably of six to 10 carbon atoms such as, for example, "phenyl, tolyl" and the like. The term "aralkyl" encompasses a lower alkyl group as defined in which an aryl group as defined is substituted for a hydrogen such as benzyl, phenethyl and the like. The term "acyl" denotes the redical derived from a carboxylic acid, preferably "lower alkanoyl and monocyclic aryl carboxylic acids, e.g., benzoic and toluic acids."

According to the process of this invention, a quaternary salt of a 2-substituted-1,2,3,4-tetrahydro-Y-carboline of Formula II is reacted with an anion X⁻ to give the title compound I. The X⁻ is utilized as the commercially available alkali metal salt (i.e., sodium cyanide and sodium phenylsulfinate) or is prepared in situ by treatment of the corresponding conjugate acid (commercially available) with a base.

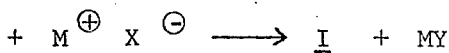

Y is an anion such as Cl⁻, Br⁻, I⁻, SO$_4$⁻

M is an alkali metal such as Na, K.

The reaction may be carried out in a variety of solvents such as water, methanol, dimethylformamide, dimethylformamide-tetrahydrofuran mixture, or hexamethylphosphortriamide. The reaction temperature can vary between room temperature (25°C) and 100°C and the reaction time can vary between 1 hour and 65 hours.

The choice of solvent depends on the stability and the reactivity of the anion in question.

Anions (X⁻)

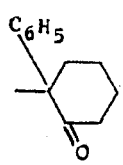

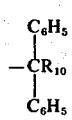

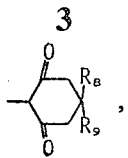

and —CH(SO₂C₆H₅)₂ which are stable in an aqueous solution, are prepared by treatment of the conjugate acid (active methylene compound) with an alkali hydroxide using water as the solvent. These anions as well as the commercially available CN⁻ are reacted with II by refluxing in aqueous solution.

The anion (X⁻), —CH(CO₂CH₃)₂ is readily prepared from its conjugate acid (dimethyl malonate) by the use of sodium methoxide in methanol and reaction with II is carried out by refluxing in the latter solvent.

Some of the anions (X⁻) are best prepared from their respective conjugate acids by the use of a base such as sodium hydride in a non-hydroxylic solvent such as tetrahydrofuran or dimethylformamide.

Examples are

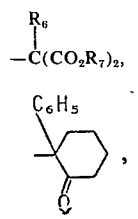

After the formation of these anions, a solution of II in a solvent such as dimethylformamide is added and the mixture is stirred at room temperature.

The anions, (X⁻) —SO₂C₆H₅ and

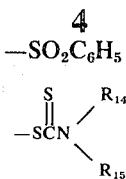

are commercially available as their sodium salts. These are best reacted by heating on a steam bath with II in a solvent such as hexamethyphosphortriamide.

The starting 1,2,3,4-tetrahydro-γ-carbolines are prepared by preocedures known to the art [See V. Boekelheide, et al., JACS, 72, 2132 (1950), C. J. Cattanach, et al., J. Chem. Soc. (C) 1235 (1968)]. They are readily converted to the corresponding quaternary salts by treatment of the free base with an alkyl halide.

The compounds I wherein R₁ is hydrogen can be alkylated on the indole nitrogen to give compounds of formula I where R₁ is alkyl or aralkyl. The procedure involves conversion of the N-unsubstituted compound to its sodium salt using a base such as sodium amide in liquid ammonia and treatment of this salt with an alkyl or aralkyl halide or alkyl or aralkyl sulfate.

Compounds of formula I wherein X is —CONH₂ are prepared by treatment of a compound of formula I wherein X is CN with an acid such as hydrochloric acid.

Compounds of formula I wherein X is CO₂R₁₃ are prepared by treatment of a compound of formula I wherein X is CN with an alcohol of formula R₁₃OH in the presence of an acid such as hydrogen chloride.

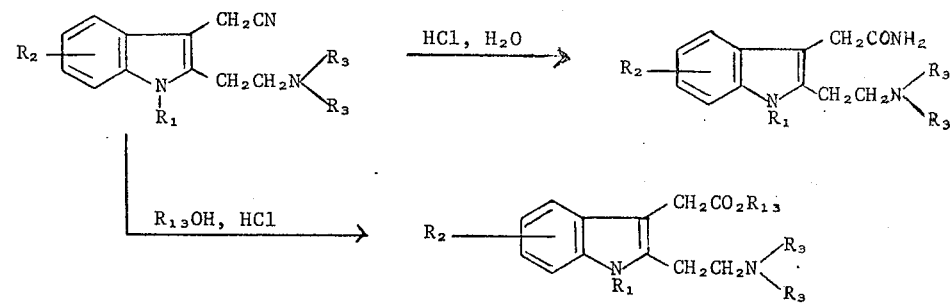

Compounds of formula I wherein X is

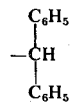

are prepared by treatment of a compound of formula I wherein X is

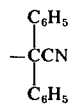

with an organometallic reagent such as methyllithium.

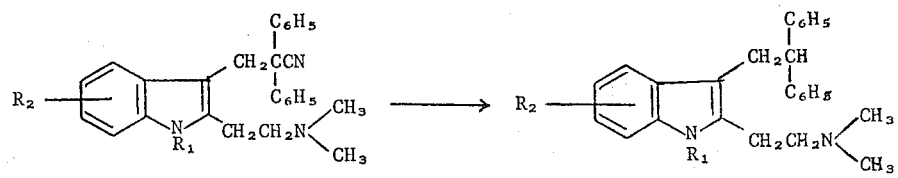

The compounds of this invention form salts with pharmaceutically acceptable acids and these salts are included within the scope of this invention. These salts include, for example, salts formed with hydrochloric, hydrobromic, sulfuric, nitric, acetic acids and the like.

The above compounds and their salts exhibit central nervous system depressing activity. For example, when administered intraperitoneally to rodents such as mice at a dose of 10–100 mg/kg, sedation of the mice is produced. These compounds were further evaluated in other animal models, e.g., isolated fighting mice and killer rats, and were found to reduce agression, in the same dose range.

These compounds are useful as mild sedatives or anti-aggression agents, within the above-described dose range.

To further illustrate the practice of this invention, the following examples are included, the temperatures indicated therein being in degrees Centigrade:

EXAMPLE 1

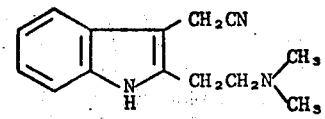

2-[2-(Dimethylamino)ethyl]indole-3-acetonitrile

To a solution of 4.9 g (0.1 mol) of sodium cyanide in 500 ml of water was added (as the dry powder) 32.8 g (0.1 mol) of 2-methyl-1,2,3,4-tetrahydro-γ- carboline methiodide, the reaction mixture was refluxed for 3 hr, and was allowed to stand at room temperature. The aqueous supernatant was poured away from the solid which had precipitated and the latter was partitioned between dichloromethane and water. The dried (Na$_2$SO$_4$) dichloromethane layer was evaporated to give 17.4 g of product, mp 122°–127°. Recrystallization from methanol gave 15 g of material, mp 129°–131°.

Anal. Calcd for Ch$_{14}$H$_{17}$N$_3$: C, 73.97; H, 7.54; N, 18.49. Found: C, 73.85; H, 7.56; N, 18.21.

EXAMPLE 2

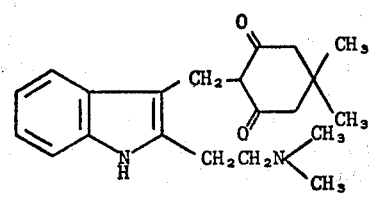

2-({2-[2-(Dimethylamino)ethyl indol-3-yl}methyl)-5,5-dimethyl-1,3-cyclohexanedione The same reaction procedure was carried out using the anion formed by the addition of 14.0 g (0.1 mol) of dimedone to 100 ml of 1N sodium hydroxide. Reflux time was 5 hr. The white crystalline solid which separated from the reaction mixture was collected by filtration, washed successively with 100 ml of saturated sodium carbonate solution and 100 ml of water, and recrystallized from 300 ml of methanol to give 20.4 g of product, mp 157°–160°dec.

Anal. Calcd for C$_{21}$H$_{28}$N$_2$O$_2$: C, 74.08; H, 8.29; N, 8.23. Found: C, 73.90; H, 8.48; N, 8.02.

EXAMPLE 3

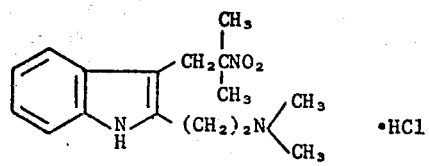

2-[2(Dimethylamino)ethyl]-3-(2-methyl-2-nitropropyl)indole Hydrochloride

The same reaction procedure was carried out using the anion formed by the addition of 9.0 g (0.1 mol) of 2-nitropropane to 100 ml of 1N sodium hydroxide. The reflux time was 1 hour. Evaporation of the dichloromethane extraction solvent gave a residue which was dissolved in ether and treated with excess ethereal hydrogen chloride to cause precipitation of 10.9 g of the hydrochloride salt, mp 222°–226°dec. Recrystallization from isopropyl alcohol gave 8.4 g of material, mp 224°–226°dec.

Anal. Calcd for C$_{16}$H$_{23}$N$_3$O$_2$.HCl: C, 58.98; H, 7.42; N, 12.90; Cl, 10.88. Found: C, 59.08; H, 7.47; N, 12.72; Cl, 10.77.

EXAMPLE 4

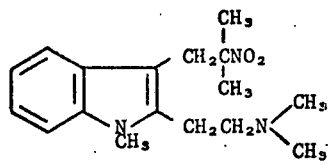

1-Methyl-2-[2(dimethylamino)ethyl]-3-(2-methyl-2-nitropropyl)indole

The same reaction procedure was carried using the anion from 9.0 g (0.1 mol) of 2-nitropropane and 46.8 g (0.1 mol) of 2,5-dimethyl-1,2,3,4-tetrahydro-γ-carboline, the reflux time being 22 hr. The reaction mixture was extracted with ether and the ether solution was washed successively with water and saturated sodium chloride solution. The residue obtained on evaporation of the solvent was recrystallized from hexane to give 11 g of product, mp 87°–90°.

Anal. Calcd for C$_{17}$H$_{25}$N$_3$O$_2$: C, 67.30; H, 8.31; N, 13,85. Found: C, 67.10; H, 8.32; N, 13.89.

EXAMPLE 5

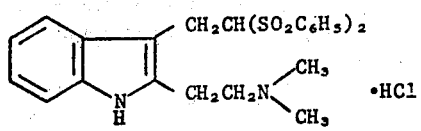

N,N-Dimethyl-3-[2,2-bis(phenylsulfonyl)ethyl]-1H-indole-2-ethanamine Hydrochloride The same reaction procedure was carried out using the anion derived from 29.6 g (0.1 mol) of bis-phenylsulfonylmethane and 32.8 g (0.1 mol) of 2-methyl-1,2,3,4-tetrahydro-γ-carboline, methiodide. The reflux time was 2 hr and the extraction solvent was ethyl acetate. The residue obtained on evaporation of the ethyl acetate was dissolved in 500 ml of tetrahydrofuran and treated with ethereal hydrogen chloride. The resulting crude hydrochloride salt was recrystallized from 400 ml of 95% ethanol to give 31.5 g of product, mp 236°–238°dec.

Anal. Calcd for $C_{26}H_{28}N_2O_4S_2 \cdot HCl$: C, 58.58; H, 5.48; Cl, 6.65; N, 5.26; S, 12.03. Found: C, 58.52; H, 5.57; Cl, 6.37; N, 4.97; S, 12.15.

EXAMPLE 6

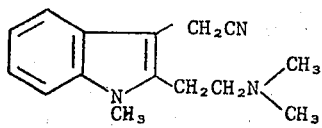

2-[(2-Dimethylamino)ethyl]-1-methylindole-3-acetonitrile

The same reaction procedure was carried out using 2.0 g (0.04 mol) of sodium cyanide and 6.8 g (0.02 mol) of 2,5-dimethyl-1,2,3,4-tetrahydro-γ-carboline methiodide. The reflux time was 20 hr and the extraction solvent was ether. The residue obtained on evaporation of the ether was recrystallized from 10 ml of isopropyl alcohol to give 0.42 g of product, mp 77°–79°.

EXAMPLE 7

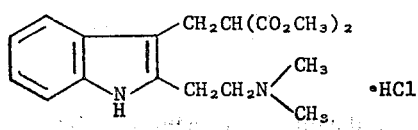

Dimethyl({2-[2-Dimethylamino)ethyl]indol-3-yl}-methyl) malonate, Hydrochloride

To the anion prepared from 13.2 g (0.1 mol) of dimethyl malonate, 5.9 g (0.11 mol) of sodium methoxide, and 400 ml of methanol was added 32.8 g (0.1 mol) of 2-methyl-1,2,3,4-tetrahydro-γ-carboline (as the powder) and the reaction mixture was refluxed for 4 hr. The solvent was removed in vacuo, the residue was treated with ice-water, and the supernatant was decanted from the resulting gum. The gum was dissolved in 400 ml of dichloromethane. Evaporation of the dried dichloromethane solution gave an oily residue which was dissolved in 350 ml of ether. Treatment with ethereal hydrogen chloride resulted in precipitation of the slightly hygroscopic hydrochloride salt. Recrystallization from 350 ml of isopropyl alcohol gave 20.0 g of product, mp 193°–195°dec.

Anal. Calcd for $C_{18}H_{24}N_2O_4 \cdot HCl$: C, 58.61; H, 6.83; Cl, 9.61; N, 7.59. Found: C, 58.46; H, 7.10; Cl, 9.51; N, 7.42.

EXAMPLE 8

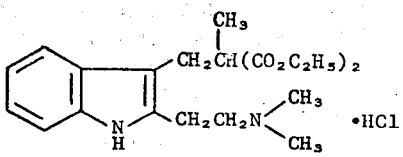

Diethyl({2-[2-(Dimethylamino)ethyl]indol-3-yl}-methyl)methylmalonate Hydrochloride To the anion prepared from 17.4 g (0.1 mol) of diethyl methylmalonate, 0.105 mol of sodium hydride, and 150 ml of tetrahydrofuran was added a solution of 32.8 g (0.1 mol) of 2-methyl-1,2,3,4-tetrahydro-γ-carboline methiodide in 400 ml of dimethylformamide. The reaction mixture was stirred at room temperature for 65 hr, the solvent was removed in vacuo, the residue was treated with ice-water and the supernatant was decanted from the resulting gum. This was partitioned between ether and water. The ether solution was washed successively with water and saturated aqueous sodium chloride solution, dried over sodium sulfate, filtered, and treated with ethereal hydrogen chloride. The resulting crude hydrochloride salt was collected and recrystallized from 220 ml of isopropyl alcohol to give 24.2 g of product, mp 150°–152°.

Anal. Calcd for $C_{21}H_{30}N_2O_4 \cdot HCl$: C, 61.38; H, 7.60; Cl, 8.62; N, 6.82. Found: C, 61.37; H, 7.58; Cl, 8.83; N, 6.84.

EXAMPLE 9

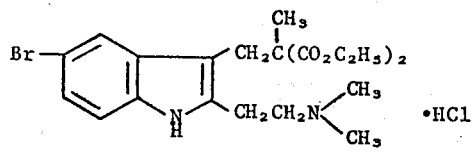

Diethyl({5-Bromo-[2-(dimethylamino)ethyl]indol-3-yl}-methyl) methylmalonate, Hydrochloride The same procedure was used with 17.4 g (0.1 mol) of diethyl methylmalonate and 40.8 g (0.1 mol) of 8-bromo-2-methyl-1,2,3,4-tetrahydro-γ-carboline methiodide. The crude hydrochloride salt was recrystallized from 150 ml of isopropyl alcohol to give 34.6 g of product, mp 146°–148°.

Anal. Calcd for $C_{21}H_{29}BrN_2O_4 \cdot HCl$: C, 51.49; H, 6.17; Br, 16.31; Cl, 7.24; N, 5.72. Found: C, 51.51; H, 6.31; Br, 16.60; Cl, 7.11; N, 5.71.

EXAMPLE 10

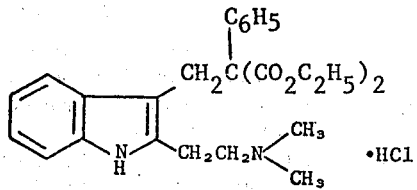

Diethyl({2-[2-(Dimethylamino)ethyl]indol-3-yl}-
methyl)phenylmalonate, Hydrochloride The same procedure was employed with 23.8 g (0.1 mol) of 2-methyl-1,2,3,4-tetrahydro-γ-carboline methiodide. The crude hydrochloride salt was recrystallized from 110 ml of acetonitrile to give 30.7 g of product, mp 188°–190°.

Anal. Calcd for $C_{26}H_{32}N_2O_4 \cdot HCl$: C, 66.02; H, 7.03; Cl, 7.50; N, 5.92. Found: C, 66.28; H, 7.03; Cl, 7.58; N, 5.78.

EXAMPLE 11

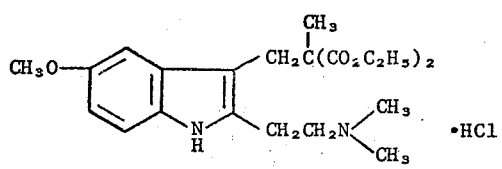

Diethyl({2-[2-(dimethylamino)ethyl]-5-methoxyindol-3-yl}methyl) methylmalonate, Hydrochloride The same procedure was employed with 17.4 g (0.1 mol) of diethyl methylmalonate and 35.6 g (0.1 mol) of 8-methoxy-2-methyl-1,2,3,4-tetrahydro-γ-carboline methiodide, the reaction time being 24 hr. The crude hydrochloride salt was recrystallized from 150 ml of isopropyl alcohol to give 22.3 g of product, mp 162°–163°.

Anal. Calcd for $C_{22}H_{32}N_2O_5 \cdot HCl$: c, 59.92; H, 7.54; Cl, 8.04; N, 6.35. Found: C, 59.70; H, 7.65; Cl, 8.03; N, 6.54.

EXAMPLE 12

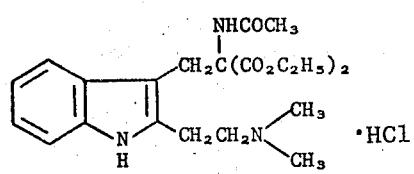

Diethyl Acetamido({2-[2-(dimethylamino)ethyl]indol-3-yl methyl)}malonate, Hydrochloride The same procedure was employed with 21.7 g (0.1 mol) of diethyl acetamidomalonate and 32.8 g (0.1 mol) of 2-methyl-1,2,3,4-tetrahydro-γ-carboline except that the anion was prepared in 400 ml of dimethylformamide rather than tetrahydrofuran and the reaction time was 20 hr. The crude hydrochloride salt was recrystallized from 500 ml of acetonitrile to give 18.8 g of product, mp 205°–207°dec.

Anal. Calcd for $C_{22}H_{31}N_3O_5 \cdot HCl$: C, 58.21; H, 7.11; Cl, 7.81; N, 9.26. Found: C, 58.45; H, 7.08; Cl, 7.74; N, 9.34.

EXAMPLE 13

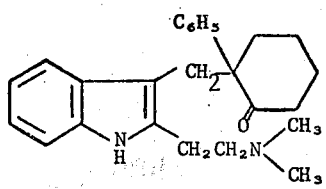

2-({2-[2-(Dimethylamino)ethyl]indol-3yl)}methyl)-2-phenylcyclohexanone

To the anion prepared from 17.4 g (0.1 mol) of 2-phenylcyclohexanone, 0.105 mol of sodium hydride, and 300 ml of tetrahydrofuran was added a solution of 32.8 g (0.1 mol) of 2-methyl-1,2,3,4-tetrahydro-γ-carboline in 600 ml of dimethylformamide and the reaction mixture was stirred at room temperature for 20 hr. The solvent was removed in vacuo, the residue was treated with ice water, and the resulting brown precipitate was collected and dissolved in 600 ml of dichloromethane. This solution was washed well with water, dried, and evaporated to dryness. The residue was triturated with 400 ml of ether to give 26.0 g of material, mp 171°–175°. Recrystallization from 600 ml of isopropyl alcohol gave 21.6 g of product, mp 176°–179°.

Anal. Calcd for $C_{25}H_{30}N_2O$: C, 80.17; H, 8.07; N, 7.48. Found: C, 79.96; H, 7.98; N, 7.39.

EXAMPLE 14

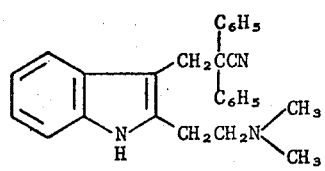

2-[2-(Dimethylamino)ethyl]-α,α-diphenylindole-3-propionitrile

The same reaction procedure was carried out using 19.3 g (0.1 mol) of diphenylacetonitrile. After the ice-water treatment, the resulting solid was collected and dissolved in 1800 ml of ethyl acetate. This solution was successively washed well with water and saturated aqueous sodium chloride solution, dried, and evaporated to dryness. The residue was recrystallized from 180 ml of ethyl acetate to give 29.8 g of product, mp 181°–185°. Recrystallization gave an analytical sample, mp 183°–186°.

Anal. Calcd for $C_{27}H_{27}N_3$: C, 87.40; H, 6.92; N, 10.68. Found: C, 82.14; H, 7.10; N, 10.63.

EXAMPLE 15

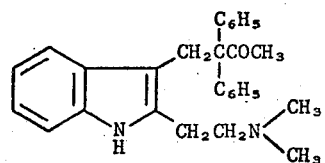

4-{2-[2-(Dimethylamino)ethyl]indol-3-yl}-3,3-diphenyl-2-butanone

To the anion prepared from 21.0 g (0.1 mol) of 1,1-diphenylacetone and 0.1 mol of sodium hydride in 250 ml of dimethylformamide was added a solution of 32.8 g of 2-methyl-1,2,3,4-tetrahydro-γ-carboline methiodide in 400 ml of dimethylformamide and the reaction mixture was stirred at room temperature for 65 hr. The solvent was removed in vacuo and the residue was partitioned between water and ether. The ether layer was washed well with water, dried and evaporated to dryness. Recrystallization of the residue from cyclohexane gave 24 g of product, mp 135°–137°.

Anal. Calcd for $C_{28}H_{30}N_2O$: C, 81.91; H, 7.37; N, 6.82. Found: C, 82.03; H, 7.43; N, 6.79.

EXAMPLE 16

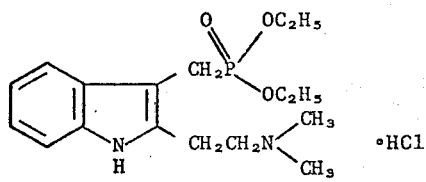

Diethyl({2-[2-(Dimethylamino)ethyl]indol-3yl}-methyl)phosphonate hydrochloride.

To the anion prepared from 15.7 g (0.1 mol) of diethyl phosphite, 0.1 mol of sodium hydride, and 100 ml of tetrahydrofuran was added a solution of 32.8 g (0.1 mol) of 2-methyl-1,2,3,4-tetrahydro-γ-carboline methiodide in 350 ml of dimethyl formamide and the reaction mixture was stirred at room temperature for 20 hr. The solvent was removed in vacuo and the residue was partitioned between dichloromethane and water. The washed dichloromethane solution was dried over sodium sulfate, evaporated to dryness, and the residue was dissolved in 350 ml of ether. The filtered ether solution was treated with ethereal hydrogen chloride and the precipitated hydrochloride salt (32 g, mp 132–°) was recrystallized from 180 ml of acetonitrile to give 12.5 g of product, mp 150–152°.

Anal. Calcd for $C_{17}H_{27}N_2PO_3 \cdot HCl$: C, 54,57; H, 7.52; Cl, 9.46; N, 7.47; P, 8.26. Found: C, 54.26; H, 7.34; Cl, 9.24; N, 7.41; P, 8.09.

EXAMPLE 17

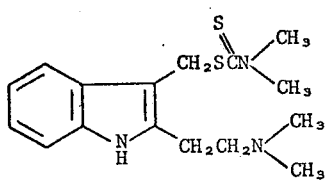

{2-[2-(dimethylamino)ethyl]-1H-indol-3-yl}methyl dimethylcarbamodithioate

A mixture of 6.56 g (0.02 mol) of 2-methyl-1,2,3,4-tetrahydro-γ-carboline methiodide, 3.9 g (0.022 mol) of sodium dimethyditihiocarbamate dihydrate, and 30 ml of hexamethylphosphortriamide was heated on a steam bath for 3 hr, allowed to cool to room temperature, poured into 400 ml of water, and extracted with 700 ml of ether. The ether solution was washed successively with water and saturated sodium chloride solution, dried over sodium sulfate and evaporated to dryness. Recrystallization of the residue from cyclohexane gave 4.1 g of product, mp 125°–128°. Another recrystallization gave an analytical sample, mp 126°–128°.

Anal. Calcd for $C_{16}H_{23}N_3S_2$: C, 59.77; H, 7.21; N, 13.07; S, 19.95. Found: C, 59.67; H, 7.03; N, 13.15; S, 19.89.

EXAMPLE 18

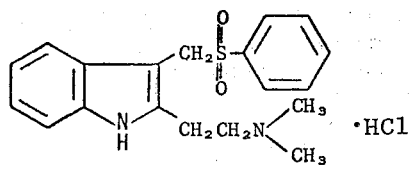

N,N-Dimethyl-3[(phenylsulfonyl)methyl]-1H-indole-2-ethanamine Hydrochloride

A mixture of 9.9 g (0.03 mol) of 2-methyl-1,2,3,4-tetrahydro-γ-carboline methiodide, 5.0 g (0.03 mol) of sodium phenylsulfinate and 50 ml of hexamethylphosphortriamide was heated on a steam bath for 4 hr, allowed to cool to room temperature, poured into 400 ml of water and extracted with 600 ml of ethyl acetate. The ethyl acetate solution was washed successively with water and saturated sodium chloride solution, dried over sodium sulfate and treated with ethereal hydrogen chloride. The precipitated hydrochloride salt was recrystallized from 250 ml of acetonitrile to give 4.9 g of product, mp 202°–205°dec.

Anal. Calcd for $C_{19}H_{21}N_2O_2S \cdot HCl$: C, 60.23; H, 6.12; Cl, 9.36; N, 7.39; S, 8.46. Found: C, 60.10; H, 6.23; Cl, 9.16; N, 7.37; S, 8.41.

EXAMPLE 19

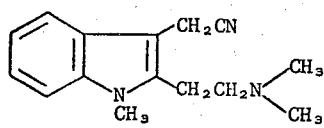

2-[(2-Dimethylamino)ethyl]-1-methylindole-3-acetonitrile

Sodamide was prepared by portionwise addition of 2.53 g (0.11 mol) of sodium to 300 ml of liquid ammonia containing a pinch of ferric nitrate nonahydrate. A solution of 22.7 g (0.1 mol) of 2[2-(dimethylamino)ethyl]indole-3-acetonitrile in 300 ml of dimethylformamide was added, the mixture was stirred at −78° for 1 hr, and a solution of 15.6 g (0.11 mol) of methyl iodide in 50 ml of dimethylformamide was added. The mixture was allowed to warm slowly to 25°, the ammonia was evaporated, the residue was stirred with 500 ml of water, and then extracted with 500 ml of ether. The ether layer was washed successively with water and saturated sodium chloride solution, dried over sodium sulfate, and evaporated to dryness. Recrystallization of the residue from isopropyl alcohol gave 8.0 g of product, mp 77°–79°.

Anal. Calcd for $C_{15}H_{19}N_2$: C, 74.65; H, 7.94; N, 17.41. Found: C, 74.81; H, 7.92; N, 17.33.

EXAMPLE 20

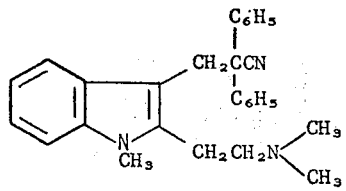

1-Methyl-2-[2-(dimethylamino)ethyl]-α,α-diphenylindole-3-propionitrile

The same procedure was used to methylate 39.6 g (0.1 mol) of 2-[2-dimethylamino)ethyl]-α, α-diphenylindole-3-propionitrile. The residue obtained on evaporation of the ethereal extraction solvent was recrystallized from 300 ml of isopropyl alcohol to give 30.6 g of product, mp 133°–136°.

Anal. Calcd for $C_{28}H_{29}N_3$: C, 82.52; H, 7.17; N, 10.31. Found: C, 81.32; H, 7.19; N, 10.21.

EXAMPLE 21

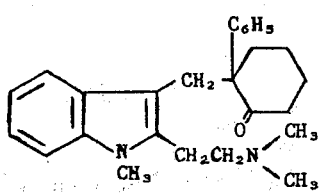

2-({2-[2-(Dimethylamino)ethyl]-1-methylindol-3-yl}-methyl)-2-phenylcyclohexanone Hydrochloride The same procedure was used to methylate 37.5 g (0.1 mol) of 2({2-[2-(dimethylamino)ethyl]indol-3-yl}methyl)-2-phenylcyclohexanone. The residue obtained on evaporation of the ethereal extraction solvent was redissolved in ether and treated with ethereal hydrogen chloride. The crude hydrochloride salt was collected and recrystallized from 750 ml of isopropyl alcohol to give 25.8 g of product, mp 246°–247°dec.

Anal. Calcd for $C_{26}H_{32}N_2O.HCl$: C, 73.48; H, 7.83; Cl, 8.34 N, 6.59. Found: C, 73.24; H, 7.96; Cl, 8.35; N, 6.53.

EXAMPLE 22

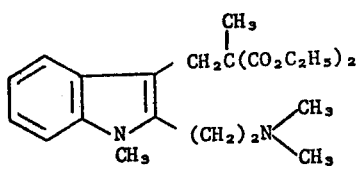

Diethyl ({2-[2-(dimethylamino)ethyl]-1-methylindol-3-yl}methyl)methyl malonate hydrochloride.

A solution of 41.1 g (0.1 mol) of diethyl ({2-[2-(dimethylamino)ethyl]indol-3-yl}-methyl)methylmalonate hydrochloride in 1000 ml of water was treated with 100 ml of 1N sodium hydroxide and the mixture was extracted with 750 ml of ether. The ether solution was washed successively with water saturated sodium chloride solution, dried over sodium sulfate and evaporated to dryness to give 37 g of the free base as a colorless gum. This was methylated, using the same procedure described for the previous example. The crude hydrochloride salt was recrystallized from 500 ml of isopropyl alcohol to give 28.5 g of product, mp 194°–198° dec.

Anal. Calcd for $C_{22}H_{32}N_2O_4.HCl$: C, 62.18; H, 7.83; Cl, 8.34; N, 6.59. Found: C, 62.24; H, 7.70; Cl, 8.16; N, 6.48.

EXAMPLE 23

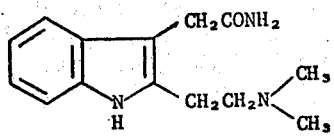

2-[2-(Dimethylamino)ethyl]indole-3-acetamide

A mixture of 9.1 g (0.04 mol) of 2[2-dimethylamino)ethyl]indole-3-acetonitrile and 80 ml of concentrated hydrochloric acid was stirred at 50° for 1 hr. It was diluted with ice-water, made alkaline to pH 9, and extracted with dichloromethane. The residue obtained on evaporation of the dichloromethane was triturated with 600 ml of ethyl acetate. The filtered ethyl acetate solution was evaporated to give a residue which was recrystallized from 40 ml of benzene to give 4.9 g of product, mp 114°–117°.

Anal. Calcd for $C_{14}H_{19}N_3O$: C, 68.54; H, 7.81; N, 17.13. Found: C, 68.42; H, 7.95; N, 16.99.

EXAMPLE 24

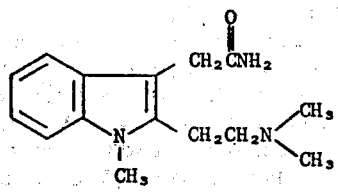

2-[2-(Dimethylamino)ethyl]-1-methylindole-3-acetamide

The same procedure was employed using 9.6 g (0.04) mol of 1-methyl-2[2-(dimethylamino)ethyl]indole-3-acetonitrile. The crude product was purified by dissolving in 250 ml of ethyl acetate and concentrating to a volume of 50 ml to give 6.7 g of material, mp 131°–134°. Another recrystallization gave an analytical sample, mp 134°–136°.

Anal. Calcd for $C_{15}H_{21}N_3O$: C, 69.46; H, 8.16; N, 10.21. Found: C, 69.49; H, 8.25; N, 15.91.

EXAMPLE 25

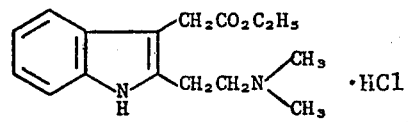

Ethyl 2-[2-(Dimethylamino)ethyl]indole-3-acetate, Hydrochloride

Hydrogen chloride gas was bubbled through a solution of 13.6 g (0.06 mol) of 2[2-(dimethylamino)ethyl]indole-3-acetonitrile in 450 ml of ethanol. Addition of the gas was continued for 4 hr during which time the reaction mixture became heated to reflux temperature. It was then stirred at room temperature for 20 hr, poured into icewater, made alkaline to pH 9, and quickly extracted with dichloromethane. Evaporation of the dichloromethane solution gave an oily residue which was dissolved in ether and treated with ethereal hydrogen chloride. The resulting crude hydrochloride salt (3.5 g, mp 136°–142°) was recrystallized from ethyl acetate to give 2 g of product, mp 145°–148°.

Anal. Calcd for $C_{16}H_{22}N_2O_2 \cdot HCl$: C, 61.83, H, 7.46; Cl, 11.41; N, 9.01. Found: C, 61.79; H, 7.52; Cl, 11.30; N, 9.03.

EXAMPLE 26

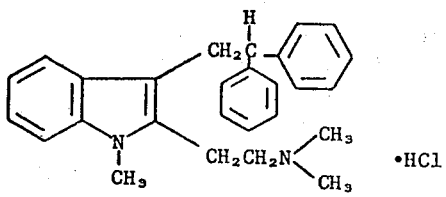

2-[2-(Dimethylamino)ethyl]-3-(2,2-diphenylethyl)-1-methylindole hydrochloride

To a solution of 0.1 mol of methyllithium in 60 ml of ether was slowly added a solution of 10.1 g (0.025 mol) of 1-methyl-2-[2-(dimethylamino)ethyl]-α,α-diphenylindole-3-propionitrile in 200 ml of benzene and the mixture was refluxed for 20 hr. It was cooled to room temperature and treated with ice-water. The layers were separated, the benzene solution was evaporated to dryness, and the residue was dissolved in ether. Treatment with ethereal hydrogen chloride gave 8.5 g of crude hydrochloride salt which was recrystallized from ethyl acetate to give 4.5 g of product, mp 194°–196°.

Anal. Calcd for $C_{27}H_{30}N_2 \cdot HCl$: C, 77.40; N, 7.46; Cl, 8.46; N, 6.69. Found: C, 77.22; H, 7.58; Cl, 8.50; N, 6.85.

A 1.0g portion of this hydrochloride salt was dissolved in 30 ml of methanol and 1N sodium hydroxide was added to basify it to a pH of 9. Dilution with water, extraction with ether, evaporation of the ether and recrystallization of the residue from 8 ml of hexane gave 0.5 g of the free base, mp 92°–94°.

Anal. Calcd for $C_{27}H_{30}N_2$: C, 84.77; H, 7.91; N, 7.32. Found: C, 84.76; H, 8.03; N, 7.14.

We claim:
1. A compound of the formula:

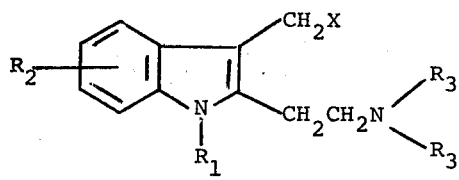

wherein $R_1$ is hydrogen, lower alkyl or phenyl lower alkyl; $R_2$ is hydrogen, lower alkyl, lower alkoxy, halogen, trifluoromethyl, cyano or nitro; $R_3$ is lower alkyl; and X is cyano.

2. A compound according to claim 1 which is 2-[2-(dimethylamino)ethyl]indole-3-acetonitrile.

3. A compound according to claim 1 which is 2-[(2-dimethylamino)ethyl]-1-methylindole-3-acetonitrile.

* * * * *